United States Patent [19]

Miller et al.

[11] Patent Number: 5,068,404

[45] Date of Patent: Nov. 26, 1991

[54] THERMAL DEALKYLATION OF N-ALKYL N-PHOSPHONOMETHYLGLYCINE

[75] Inventors: William H. Miller, Glendale; Terry M. Balthazor, University City, both of Mo.

[73] Assignee: Monsanto Company, St. Louis, Mo.

[21] Appl. No.: 501,390

[22] Filed: Mar. 26, 1990

Related U.S. Application Data

[63] Continuation of Ser. No. 329,053, Mar. 27, 1989, abandoned, which is a continuation of Ser. No. 874,752, Jun. 16, 1986, abandoned, which is a continuation of Ser. No. 687,404, Dec. 28, 1984, abandoned.

[51] Int. Cl.$^5$ .............................................. C07F 9/38
[52] U.S. Cl. ...................................... 502/17; 585/678
[58] Field of Search ........................................... 562/17

[56] References Cited

U.S. PATENT DOCUMENTS

| | | | |
|---|---|---|---|
| 2,384,817 | 9/1945 | Chitwood | 502/526 |
| 3,288,846 | 11/1966 | Irani et al. | 260/500 |
| 3,927,080 | 12/1975 | Gaertner | 260/502.5 |
| 3,956,370 | 5/1976 | Parry et al. | 260/502.5 |
| 3,969,398 | 7/1976 | Hershman | 260/502.5 |
| 4,442,041 | 4/1984 | Subramanian | 260/502.5 F |
| 4,965,403 | 10/1990 | Fields et al. | 562/17 |

FOREIGN PATENT DOCUMENTS 2363634  6/1974  Fed. Rep. of Germany ........ 562/16

OTHER PUBLICATIONS

*Protective Groups in Organic Synthesis*, Chapter 7, "Protection for the Amino Group", T. W. Green, John Wiley (1981), pp. 218–287.
S-I Murahashi et al., JACS, 101, 1729 (1979).

*Primary Examiner*—J. E. Evans
*Attorney, Agent, or Firm*—Raymond C. Loyer; Frank D. Shearin

[57] ABSTRACT

There is disclosed a process for producing the alkali metal salts of N-phosphonomethylglycine which comprises heating to an elevated temperature an aqueous solution of a di- or tri-alkali metal salt of N-alkyl-N-phosphonomethylglycine. The N-alkyl substituent contains at least one hydrogen on the beta carbon atom.

9 Claims, No Drawings

THERMAL DEALKYLATION OF N-ALKYL N-PHOSPHONOMETHYLGLYCINE

CROSS REFERENCES TO RELATED APPLICATION

This application is a continuation of application Ser. No. 329,053 filed Mar. 27, 1989, now abandoned, which is a continuation of application Ser. No. 874,752 filed June 16, 1986, now abandoned, which is a continuation of application Ser. No. 06/687,404 filed Dec. 28, 1984, now abandoned.

BACKGROUND OF THE INVENTION

This invention relates to a process for preparing N-phosphonomethylglycine by the dealkylation of an N-alkyl-N-phosphonomethylglycine. More particularly, the invention relates to a relatively simple method whereby N-phosphonomethylglycine is produced in high yield and yet relatively free of reaction by-products.

N-Phosphonomethylglycine, known also by its common name glyphosate, is a highly effective and commercially important phytotoxicant useful in controlling a large variety of weeds and crops. It is applied to the foliage of a very broad spectrum of perennial and annual grasses and broad-leafed plants. Industrial uses include control of weeds along roadsides, waterways, transmission lines, in storage areas, and in other nonagricultural areas. Usually glyphosate is formulated into herbicidal compositions in the form of its various salts which retain the anionic form of glyphosate in solution, preferably in water.

Because of its commercial importance, many processes for making glyphosate have been published. One process for the manufacture of glyphosate is described by Hershman in U.S. Pat. No. 3,969,398. In said process iminodiacetic acid is reacted with formaldehyde and phosphorous acid to produce an intermediate N-phosphonomethyliminodiacetic acid. This intermediate is oxidized to produce glyphosate.

Another process for the manufacture of glyphosate is described by Gaertner in U.S. Pat. No. 3,927,080. Gaertner describes the production of glyphosate wherein N-t-butyl-N-phosphonomethylglycine or its esters are hydrolyzed under acidic conditions.

The chemistry of the carbon/nitrogen bond of amines has been the subject of study in recent years. For example, Murahashi and Watanabe disclosed the metal catalyzed reaction of tertiary amines with water in an article entitled "Palladium Catalyzed Hydrolysis of Tertiary Amines with Water" published in the *Journal of the American Chemical Society*, 101, 7429 (1979). In this publication it was reported that catalytic oxidation of tertiary amines proceeded generally and efficiently with palladium catalysts to provide secondary amines and carbonyl compounds.

In European Patent No. 0,055,695, there is disclosed a process for splitting off a substituent group from the nitrogen atom of an N-substituted N-phosphonomethylglycine by hydrogenolysis. The N-substituent is described as a 1-arylalkyl group suitable for hydrogenolytic cleavage. The hydrogenolytic process is carried out in the presence of a catalyst, such as platinum or palladium on barium sulfate.

SUMMARY OF THE INVENTION

In accordance with the present invention, there is provided a process for producing the alkali metal salts of N-phosphonomethylglycine which comprises heating to an elevated temperature an aqueous solution of a di- or tri-alkali metal salt of an N-alkyl-N-phosphonomethylglycine (NANP) wherein the N-alkyl group contains at least one hydrogen atom on the beta carbon. One characteristic of the reaction is the production of an olefin by-product in addition to the desired salt. When one of the other beta substituents is a hetero atom, such as nitrogen, oxygen, or sulfur, the olefin by-product may be transient and removed in a different form.

DETAILED DESCRIPTION OF THE INVENTION

The alkyl substituent of NANP employed in the process of this invention is any straight or branched chain alkyl or cycloalky group which provides a beta carbon atom having at least one hydrogen atom attached thereto, such as ethyl, propyl, isopropyl, butyl, hexyl, cyclohexyl, and cyclopropyl. The preferred alkyl substituent is represented by the formula

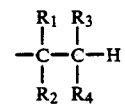

wherein $R_1$, $R_2$, $R_3$, and $R_4$ are independently selected from the group consisting of hydrogen, alkyl $C_{1-6}$, benzyl, aryl, substituted aryl, and $R_3$ and $R_4$ can also be independently selected from

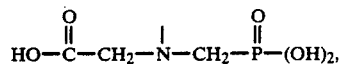

halogens, OH, alkoxy $C_{1-4}$, aryloxy, SH, thioalkyl $C_{1-4}$, thioaryl, $-NR_5R_6$ wherein $R_5$ and $R_6$ are independently selected from hydrogen, alkyl $C_{1-4}$ and aryl, provided that only one of $R_3$ and $R_4$ is

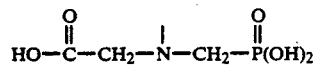

The term halogen as employed herein includes all members of the class, i.e., chlorine, fluorine, bromine, and iodine.

The term aryl as employed herein includes groups such as phenyl, naphthyl, biphenylyl, or phenyl, naphthyl, or biphenylyl substituted with from 1 to 3 substituents independently selected from the class consisting of lower alkyl, lower alkoxy, methylenedioxy, halogen, cyano, nitro, haloalkyl $C_{1-4}$, and thioalkyl.

Illustrative of the substituted phenyl groups are mono-substituted phenyl wherein the substituent is in the ortho, meta, or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl and the like, and the di- and tri-substituted phenyl groups wherein the substituents are the same or different and are located in the 2, 3, 4, 5, or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethyl-thio)phenyl, trimethylphenyl, trichlorophenyl, tributylphenyl, ethyldichlorophenyl and the like.

Groups representative of a substituted naphthyl group include methylnaphthyl, nitronaphthyl, bromonaphthyl, dimethylnaphthyl, difluoronaphthyl, trimethylnaphthyl and the like.

Groups representative of substituted biphenylyl groups include methylbiphenylyl, nitrobiphenylyl, bromobiphenylyl, dimethylbiphenylyl, difluorobiphenylyl, trimethylbiphenylyl and the like.

The term aryloxy as employed herein includes the above-mentioned aryl groups when joined by an oxygen linkage in the above-described formula, and similarly the term thioaryl as employed herein includes the above-mentioned aryl groups when joined by a sulfur linkage to the above-described formula.

The term thioalkyl as employed herein includes the above-described alkyl groups when joined to the above-described formula by a sulfur linkage.

Typical examples of $-NR_5R_6$ included within the scope of this invention are dimethylamine, methylethylamine, phenylmethylamine, diethylamine and the like.

As mentioned above, the di- or tri-alkali metal salt of an NANP is provided in aqueous solution for the process of this invention. The molar ratio of alkali metal base to NANP in the reaction mixture is generally in the range of from about 2 to 4 or more moles of alkali metal base to 1 mole of NANP. In a preferred embodiment of this invention, the molar ratio of alkali metal base to NANP is in the range of about 3 to 1 to 3.5 to 1 and preferably about 3.1 to 3.3, respectively.

The di- or tri-alkali metal salt of NANP can be provided by preforming the salt by combining NANP with an appropriate amount of base. The preformed salt is then added to water or an aqueous base for use in this invention. Alternatively, the desired alkali metal salt is formed in situ by combining an NANP or a hydrolyzable derivative of NANP with an appropriate amount of an aqueous alkali metal base and the solution heated directly resulting in a reaction which eliminates the N-alkyl group from the NANP.

The salts of the NANP typically employed are the alkali metal salts. Examples of such salts are sodium, potassium, and lithium. Preferably, the sodium salt is employed in the process of this invention. In operation, the salts are preferably provided in situ by adding sufficient base to the reaction vessel to provide the salt as will be illustrated by the examples below.

As noted above, the alkali metal salts of NANP employed in the process of this invention are derived from NANP or a hydrolyzable derivative of NANP. Because the process of this invention is performed at elevated temperatures under relatively strongly basic conditions, many different hydrolyzable NANP derivatives can be employed. Such derivatives can be employed because when combined with an aqueous base in accordance with this invention, hydrolysis takes place to form the desired alkali metal salt. Examples of such NANP derivatives are esters, amides, strong acid salts, nitriles, thioesters, and mixtures thereof. Typical examples of said hydrolyzable derivatives of NANP are known in the prior art as, for example, U.S. Pat. No. 3,799,758 to Franz, which patent is hereby incorporated by reference.

The salt of N-phosphonomethylglycine produced by the process of this invention is readily converted to the acid, N-phosphonomethylglycine, as for example, by acidification with mineral acids as is well known in the art.

While the process of this invention proceeds throughout a wide range of temperatures, typically in the range of above about 200° C., it is preferred to operate the process of this invention in the range of from about 250° C. to about 350° C. Generally, the upper limit of the temperature range in the operation of the process of this invention is dependent upon the thermal stability of materials employed in the reaction mixture.

In the process of this invention, water is retained in the reaction mixture by appropriate means, typically by maintaining the pressure over the reaction mixture in excess of the vapor pressure of water at the temperature of the reaction.

The NANP employed in the process of this invention in the form of an alkali metal salt is obtained by known processes. See, for example, U.S. Pat. No. 3,288,846 to Irani et al and Moedritzer et al, *J. Org. Chem.*, 31, 1603 (1966). The reactions described therein are easily adapted to provide the tertiary amines employed in the process of this invention.

The following examples serve to illustrate the process of this invention and are not intended to limit the invention in any way.

EXAMPLE 1

To a 100 ml pressure reactor constructed of Monel was added 21.1 g (0.10 mol) of N-isopropyl-N-phosphonomethylglycine, 26.2 g (0.33 mol) of 50% sodium hydroxide, and 8 ml of water. The reactor was closed and flushed with nitrogen for 20 minutes. The reactor was then sealed and heated to 300° C. for 3 hours. The excess pressure generated by the liberation of propene during the reaction was released, but the overall reactor pressure was controlled so as to retain water in the reaction mixture. After cooling and releasing the residual pressure, the viscous solution was removed from the reactor and diluted with 24 ml of water. The solution was neutralized with 27.2 ml of concentrated hydrochloric acid. N-Phosphonomethylglycine that precipitated from solution was filtered and air dried to yield 14.8 g of white crystals which, by analysis, were 95.2% pure. The mother liquors were purified by ion-exchange chromatography to provide an additional 1.63 g of N-phosphonomethylglycine. The total yield of product, then, was 97%.

In a manner similar to Example 1, N-phosphonomethylglycine was prepared by the dealkylation of other compounds. In Table I below there is shown other examples indicating the starting material (NANP by identifying only the N-substituent which is cleaved), reaction times, and yields of N-phosphonomethylglycine.

| Ex. | Starting Material | Reaction Time-Hrs. | Yield % |
|-----|-------------------|--------------------|---------|
| 2   | N-ethyl           | 4.5                | 87.7    |
| 3   | N-propyl          | 6                  | 19.9    |
| 4*  | N-cyclohexyl      | 6                  | 16.2    |
| 5   | N-sec-butyl       | 6                  | 79.6    |
| 6** | N-2-hydroxy-      | 6                  | 89.7    |

| Ex. | Starting Material | Reaction Time-Hrs. | Yield % |
|---|---|---|---|
| | ethyl | | 5 |

*The starting material was not completely dissolved before the reaction mixture was heated.
**5 equivalents of NaOH per equivalent of NANP.

EXAMPLE 7

To a pressure reactor was added 2.09 g (8.3 mmol) of methyl-N-[(dimethoxyphosphinyl)methyl]-N-isopropylglycine, 2.17 g (27.2 mmol) of 50% sodium hydroxide, and 10 ml of water. The reactor vessel was flushed with nitrogen for 15 minutes, sealed, and heated to 300° C. for 3.5 hours while the pressure was controlled to maintain water within the reactor. After cooling and release of residual pressure, the reaction mixture was removed from the reactor and diluted with 5 ml of water. This solution was acidified by the addition of 2.4 ml of hydrochloric acid and purified by ion-exchange chromatography to provide 0.27 g (20% yield) of N-phosphonomethylglycine.

EXAMPLE 8

In a 10 ml Teflon cup were mixed 1.0 g (2.7 mmol) of N,N'-ethylenebis-N-phosphonomethylglycine, 1.4 g (17.7 mmol) of 50% sodium hydroxide, and 0.5 ml of water. The cup was placed in a bath of 20 ml of 10% NaOH inside a Monel autoclave. The autoclave was flushed with nitrogen for 15 minutes, sealed, and heated to 300° C. for 6 hours. On cooling the reaction mixture was removed from the autoclave, acidified to pH 0.5 with hydrochloric acid, and heated to reflux for several minutes. The cooled reaction mixture was then purified by ion-exchange chromatography to yield 0.56 g (61.5% yield) of N-phosphonomethylglycine.

EXAMPLE 9

Preparation of N-Isopropyl-N-Phosphonomethylglycine

To a 5 L 3-necked flask fitted with a mechanical stirrer, thermometer, addition funnel, and condenser was added 363 g (2.37 mol) of N-isopropylglycine hydrochloride, 205 g (2.50 mol) of phosphorous acid, and 1.7 L of 20% HCl solution. The mixture was heated to 108° C. giving a solution. From the addition funnel 231 g (2.84 mol) of 37% formaldehyde solution was added to the hot reaction mixture over 2 hours. The resulting yellow solution was refluxed for 8.5 hours. All volatiles were removed by vacuum distillation to leave a yellow oil. The oil was dissolved in 300 ml of $H_2O$ and diluted with 500 ml of ethyl alcohol to cause precipitation of the product. The crystals were collected by filtration, washed with ethyl alcohol, and air dried to yield 322 g (64%) of N-isopropyl-N-phosphonomethylglycine. Additional product contained in the mother liquors was not isolated.

Although the invention is described with respect to specific embodiments, the details thereof are not to be construed as limitations except as to the extent indicated in the following claims.

What is claimed is:

1. A process for producing the alkali metal salts of N-phosphonomethylglycine in high yields in the absence of a catalyst, which comprises heating to above about 200° C., a basic aqueous solution of a di- or tri-alkali metal salt of N-alkyl-N-phosphonomethylglycine, wherein the N-alkyl group is selected from the group consisting of ethyl, isopropyl and secondary-butyl.

2. The process of claim 1 additionally containing the step of acidifying the salt of N-phosphonomethylglycine to provide N-phosphonomethylglycine.

3. The process of claim 1 wherein the N-alkyl group is isopropyl.

4. The process of claim 1 wherein the temperature is in the range of from about 250° C. to about 350° C.

5. The process of claim 1 wherein the di- or tri-alkali metal salt is formed in situ.

6. The process of claim 4 wherein the salt is formed in situ by combining a base selected from the group consisting of sodium hydroxide, potassium hydroxide and lithium hydroxide, and N-alkyl-N-phosphonomethylglycine in a molar ratio of from about 3 to 1 to about 3.5 to 1, respectively.

7. The process of claim 6 wherein the N-alkyl group is isopropyl.

8. The process of claim 6 wherein the base is sodium hydroxide.

9. The process of claim 6 wherein the N-alkyl group is ethyl.

* * * * *